United States Patent
Desgrandchamps et al.

(10) Patent No.: US 10,545,136 B2
(45) Date of Patent: Jan. 28, 2020

(54) METHODS FOR THE MONITORING AND PROGNOSIS OF A CANCER

(71) Applicants: ASSISTANCE PUBLIQUE HOPITAUX DE PARIS, Paris (FR); COMMISSARIAT A L'ENERGIE ATOMIQUE ET AUX ENERGIES ALTERNATIVES, Paris (FR); Université Paris Diderot—Paris 7, Paris (FR)

(72) Inventors: François Desgrandchamps, Paris (FR); Edgardo Delfino Carosella, Paris (FR); Joël Lemaoult, Melun (FR)

(73) Assignees: ASSISTANCE PUBLIQUE HOPITAUX DE PARIS, Paris (FR); COMMISSARIAT A L'ENERGIE ATOMIQUE ET AUX ENERGIES ALTERNATIVES, Paris (FR); Université Paris Diderot—Paris 7, Paris (FR)

( * ) Notice: Subject to any disclaimer, the term of this patent is extended or adjusted under 35 U.S.C. 154(b) by 148 days.

(21) Appl. No.: 15/518,864

(22) PCT Filed: Oct. 16, 2015

(86) PCT No.: PCT/EP2015/073963
§ 371 (c)(1),
(2) Date: Apr. 13, 2017

(87) PCT Pub. No.: WO2016/059195
PCT Pub. Date: Apr. 21, 2016

(65) Prior Publication Data
US 2017/0219561 A1    Aug. 3, 2017

(30) Foreign Application Priority Data
Oct. 17, 2014   (EP) .................................... 14306665

(51) Int. Cl.
| | | |
|---|---|---|
| G01N 33/53 | (2006.01) | |
| G01N 33/574 | (2006.01) | |
| G01N 33/50 | (2006.01) | |

(52) U.S. Cl.
CPC ........... *G01N 33/505* (2013.01); *G01N 33/53* (2013.01); *G01N 33/574* (2013.01); *G01N 2800/54* (2013.01)

(58) Field of Classification Search
CPC .... G01N 33/505; G01N 33/53; G01N 33/574; G01N 2800/54
See application file for complete search history.

(56) References Cited

U.S. PATENT DOCUMENTS 7,351,546 B2* 4/2008 Willmann .......... G01N 33/5002
                                                              435/287.2
2006/0046272 A1* 3/2006 Chow .................... G01N 33/80
                                                              435/7.2

FOREIGN PATENT DOCUMENTS

| WO | WO-03/078662 A1 | 9/2003 |
| WO | WO-2013/106586 A2 | 7/2013 |

OTHER PUBLICATIONS

Böhle et al., Intravesical bacillus Calmette-Guerin versus mitomycin C for superficial bladder cancer: a formal meta-analysis of comparative studies on recurrence and toxicity, J. Urol., 169(1):90-5 (2003).

(Continued)

*Primary Examiner* — Gailene Gabel
(74) *Attorney, Agent, or Firm* — Marshall, Gerstein & Borun LLP (57) ABSTRACT

The present invention relates to methods for prognosis and monitoring of a cancer, preferably bladder cancer, by measuring the proportion of $CD8^+$ T Lymphocytes expressing ILT-2 and the plasma level of soluble HLA-G. The invention (Continued)

also relates to anti HLA-G antibodies for use for treating a cancer in which tumor cells express HLA-G, preferably bladder cancer.

11 Claims, 5 Drawing Sheets

(56) References Cited

OTHER PUBLICATIONS

Ei-Chennawi et al., Expression of HLA-G in cancer bladder, The Egyptian Journal of Immunology, 12(1):57-64 (2005).
Gan et al., Tumor-specific upregulation of human leukocyte antigen-G expression in bladder transitional cell carcinoma, Hum. Immunol., 71(9):899-904 (2010).
Menier et al., Characterization of monoclonal antibodies recognizing HLA-G or HLA-E: new tools to analyze the expression of nonclassical HLA class I molecules, Hum. Immunol., 64(3):315-26 (2003).
Neuzillet et al., Diagnosis and management of adverse events occurring during BCG therapy for non-muscle invasive bladder cancer (NMIBC): Review of the Cancer Committee of the French Association of Urology, Progrès en urologie, 22:989-98 (2012). [English abstract only.].
Sauer et al., Efficacy of radiochemotherapy with platin derivatives compared to radiotherapy alone in organ-sparing treatment of bladder cancer, Int. J. Radiat. Oncol. Biol. Phys., 40(1):121-7 (1998).
Xylinas et al., Evaluation of combined oncologic and functional outcomes after robotic-assisted laparoscopic extraperitoneal radical prostatectomy: trifecta rate of achieving continence, potency and cancer control, Urol. Oncol., 31(1):99-103 (2013).
Babjuk et al., EAU guidelines on non-muscle-invasive urothelial carcinoma of the bladder, the 2011 update, Eur. Urol., 59(6):997-1008 (2011).
Babjuk et al., EAU guidelines on non-muscle-invasive urothelial carcinoma of the bladder: update 2013, Eur. Urol., 64(4):639-53 (2013).
Colonna et al., A common inhibitory receptor for major histocompatibility complex class I molecules on human lymphoid and myelomonocytic cells, J. Exp. Med., 186(11):1809-18 (1997).
Dong et al., Importance of HLA-G expression and tumor infiltrating lymphocytes in molecular subtypes of breast cancer, Hum. Immunol., 73(10):998-1004 (2012).
Extended European Search Report, European patent application No. 14306665.2, dated Apr. 24, 2015.
He et al., HLA-G expression in human breast cancer: implications for diagnosis and prognosis, and effect on allocytotoxic lymphocyte response after hormone treatment in vitro, Ann. Surg. Oncol., 17(5):1459-69 (2010).
International Search Report and Written Opinion, International Application No. PCT/EP2015/073963, dated Nov. 18, 2015.
Le Rond et al., Evidence to support the role of HLA-G5 in allograft acceptance through induction of immunosuppressive/ regulatory T cells, J. Immunol., 176(5):3266-76 (2006).
Lefebvre et al., Specific activation of the non-classical class I histocompatibility HLA-G antigen and expression of the ILT2 inhibitory receptor in human breast cancer, J. Pathol., 196(3):266-74 (2002).
Naji et al., Binding of HLA-G to ITIM-bearing Ig-like transcript 2 receptor suppresses B cell responses, J. Immunol., 192(4):1536-46 (2014).
O'Connell et al., Relationship between tumor gene expression and recurrence in four independent studies of patients with stage II/III colon cancer treated with surgery alone or surgery plus adjuvant fluorouracil plus leucovorin, Am. J. Clin. Oncol., 28(25):3937-44 (2010).
Paul et al., HLA-G expression in melanoma: a way for tumor cells to escape from immunosurveillance, Proc. Natl. Acad. Sci. USA, 95(8):4510-5 (1998).
Rebmann et al., Soluble HLA-G is an independent factor for the prediction of pregnancy outcome after ART: a German multi-centre study, Hum. Reprod., 25(7):1691-8 (2010).
Sheu et al., Clinical and biological significance of HLA-G expression in ovarian cancer, Semin. Cancer Biol., 17(6):436-43 (2007).
Sylvester et al., Predicting recurrence and progression in individual patients with stage Ta T1 bladder cancer using EORTC risk tables: a combined analysis of 2596 patients from seven EORTC trials, Eur. Urol., 49(3):466-77 (2006).
van Rhijn et al., Recurrence and progression of disease in non-muscle-invasive bladder cancer: from epidemiology to treatment strategy, Eur. Urol., 36(3):430-42 (2009).

* cited by examiner

METHODS FOR THE MONITORING AND PROGNOSIS OF A CANCER

CROSS-REFERENCE TO RELATED APPLICATIONS

This is the U.S. national phase of International Application No. PCT/EP2015/073963, filed Oct. 16, 2015, which claims the benefit of European Patent Application No. 14306665.2, filed Oct. 17, 2014.

FIELD OF THE INVENTION

The present invention relates to methods for the prognosis or for the monitoring of cancer, preferably bladder cancer.

The invention further relates to the use of anti HLA-G antibodies for the treatment of bladder cancer.

BACKGROUND OF THE INVENTION

Bladder cancer is a very common malignancy: it is the sixth most common cancer in the US. In 2012, there were an estimated 73 510 new cases of bladder cancer and 14 880 bladder cancer-related deaths in the United States.

According to the American Cancer Society, in 2014, the risk men will develop this cancer during their life is about 1 in 26 and 1 in 90 for women. It is considered as an elderly disease: 9 on 10 of the people touched by bladder cancer are over 55 years old. The main risk factors are smoking, chemical exposures (for instance to products used in the textile dye industry), genetic predisposition and certain medical treatment (as chemotherapy). Bladder cancer tends to recur and a patient needs a life-long close follow-up.

Bladder cancer can be divided into muscle invasive bladder cancer and non-muscle invasive bladder cancer (NMIBC). More than 70% of patients have NMIBC (Babjuk M. et al. (2011), Eur. Urol. 59: 997-1008). The recurrence rates of NMIBC range from 50% to 70%, and disease progression to muscle invasion over a 5-year period from 10 to 15% (Babjuk et al. (2013), Eur Urol. 64(4):639-53). Different classifications for risk of recurrence or progression have been proposed, based on the characteristics of the tumor itself (number, volume, invasion, grade). The EORTC risk tables for patient with stage Ta TI bladder cancer are the most widely used (Sylvester et al. (2006), Eur. Urol. 49: 466-477).

However from external validation analysis data, this risk tables exhibit a poor discrimination for both disease recurrence and progression in NMIBC patients. In particular, this model overestimates the risk of disease recurrence and progression in high-risk patients (Xylinas et al. (2013), Urol. Oncol. 31(1):99-103).

Thus, first, there is a need to find more accurate and enhanced methods, which would be quick and cost effective, for the prognosis of the outcome of a patient afflicted by a cancer, preferably bladder cancer, and for the monitoring of said cancer, preferably bladder cancer, particularly non-muscle invasive bladder cancer.

Second, the treatment used to treat bladder cancer depends on the type of cancer (whether it is muscle-invasive or not) and on the grade of the tumor.

Patients with muscle invasive bladder cancer are usually treated by chemotherapy and radical cystectomy or radiotherapy (Sauer et al. (1998), Int J Radiat Oncol Biol Phys., 40(1): 121-7).

The main treatments used in NMIBC are transurethral resection (TUR) and intravesical instillation with a chemotherapeutic agent or with Bacillus Calmette-Guerin (BCG) (van Rhijn et al. (2009), Eur. Urol. 56:430-442)

TUR is a surgical procedure and is also used in the diagnosis and prognosis of bladder cancer. Its goal is to observe and remove the tumor by passing a cystoscope through the urethra. Intravesical instillation consists in direct introduction of a chemotherapeutic agent or of BCG into the bladder through a catheter. Several analyses demonstrated that BCG is more effective than chemotherapy for reducing the recurrence and progression of bladder cancer, but it is more toxic (Bohle et al. (2003), J Urol. 169:90-5). The introduction of BCG via intravesical instillation produces a lot of side effects among which are infectious reactions, allergic reactions and auto-immune reactions due to the introduction of living bacteria into the bladder (Neuzillet et al. (2012), Progres en urologie, 22:989-998).

Those treatments are quite heavy to support and inconvenient for the patient. Moreover, treatment with BCG is the last option before bladder ablation.

Thus there is still a need to find more secure and bearable treatments in bladder cancer, and more particularly, there is a need to delay treatment with BCG as long as possible, so as to avoid the irreversible surgery.

SUMMARY OF THE INVENTION

The inventors have discovered that measuring and combining two specific different biomarkers, i.e. the plasma level of HLA-G on one hand and the proportion of CD8+T lymphocytes expressing ILT-2 on the other hand, would provide an accurate method for the prognosis of the outcome of a patient afflicted by bladder cancer, or for monitoring the recurrence of bladder cancer. Both biomarkers in combination indeed ensure a reliable and sensitive prognosis of the outcome of a patient afflicted by bladder cancer, particularly by NMIBC. They also ensure a reliable and sensitive monitoring of the recurrence of this pathology.

The inventors have also discovered that measuring the single proportion of $CD8^+$ T lymphocytes expressing ILT-2 would provide an accurate method for monitoring the recurrence of bladder cancer, particularly NMIBC, within a year. As shown in Example 2, this biomarker ensures a reliable and sensitive monitoring of recurrence of bladder cancer, particularly by NMIBC.

In a first embodiment, the present invention thus relates to a method for monitoring the recurrence of a cancer in a patient, comprising a step of measuring the proportion of $CD8^+$ T lymphocytes population expressing ILT-2 within the total population of CD8+ T lymphocytes in a biological sample obtained from said patient, wherein when said proportion is high, then the patient is classified as high risk.

In a second embodiment, the present invention also relates to a method for the prognosis of the outcome of a patient afflicted by a cancer, preferably bladder cancer, or for monitoring the recurrence of a cancer, preferably bladder cancer, in a patient, said method comprising:

a) a step of measuring the plasma level of soluble HLA-G in a first biological sample obtained from said patient, and b) a step of measuring the proportion of $CD8^+$ T lymphocytes population expressing ILT-2 within the total population of $CD8^+$ T lymphocytes in a second biological sample obtained from said patient.

The inventors have established that, according to the second embodiment, when the proportion of ILT2+$CD8^+$ T lymphocytes is less than 20%, then the patient is classified as non high risk. However, when the proportion of ILT2+

CD8+ T lymphocytes is more than 20% and when the plasma level of soluble HLA-G is more than 20 ng/mL, then the patient is classified as high risk.

The inventors have also discovered that measuring the proportion of natural killer T cells (NKT) expressing ILT-2 would be useful as a further marker for the prognosis of the outcome of a patient afflicted by a cancer, preferably bladder cancer, or for monitoring the recurrence of a cancer, preferably bladder cancer, in a patient. Specifically, they have established that when the proportion of NKT cells expressing ILT-2 in a sample obtained from a patient is more than 45%, then the patient is classified as high risk.

The invention further relates to an anti HLA-G antibody for use in the treatment of a cancer wherein tumor cells express HLA-G, preferably bladder cancer, particularly NMIBC.

BRIEF DESCRIPTION OF THE DRAWINGS

FIG. 1A) illustrates HLA-G expression by non-muscle-infiltrating bladder tumors. For HLA-G-positive tumors, HLA-G expression was detected in basal cells, umbrella cells, or both (no predominance). Representative images of negative, positive, and very positive tumor cells are shown for all three expression patterns.

FIG. 1B) is a table showing proportions of NHR and HR tumors being negative, positive, and very positive for HLA-G expression. Percentages calculated independently of the expression pattern defined above. NHR: N=43, HR: N=7.

FIG. 2B) is a graph showing inhibitory function of HLA-G from high risk patients. HLA-G was captured from plasma using anti-HLA-G-coated beads, and its capability to inhibit the anti-CD3-mediated T cell polyclonal activation was evaluated as described in Materials and Methods. Example shown is representative of 3 such experiments.

FIG. 3B) is a graph showing ILT4 expression by PBMC immune cell subsets from healthy donors (HD), non high risk (NHR) and high risk (HR) patients. CD4: CD3+CD4+ T cells. CD8: CD3+CD8+ T cells. NK: CD3-CD56+NK cells. NKT: CD3+CD56+ NKT cells. B: B cells. GD: gamma/delta T cells. Results are presented as percentages of ILT4-expressing cells within the indicated cell subset.

FIG. 3C) is a graph showing increased sensitivity to HLA-G-mediated T cell activation inhibition of T cells from HR patients. T cells from healthy donors (HD), non-high-risk (NHR) and high risk (HR) patients were activated using anti-CD3 or PMA/ionomycin, as indicated in Materials and Methods, in the presence or absence of 5 μg/ml recombinant HLA-G and, when indicated, 10 μg/ml blocking anti-ILT2. For anti-CD3 stimulation, activation was detected by CD25 upregulation by CD4+ T cells. For PMA/ionomycin stimulation, activation was detected by IFNG intracellular production by CD8+ T cells. Results are representative of 3 such experiments.

FIG. 4: Proposed Algorithm for Prognosis

FIG. 4 is as schematic illustration a proposed algorithm for prognosis, wherein

EORTC=European Organisation for Research and Treatment of Cancer score

SRHI=risk of relapse to the immunological profile at 1 year

HR=High risk

IR=Intermediate Risk

PPV=Positive Predictive Value

NPV=Negative Predictive Value

FIG. 5:

DETAILED DESCRIPTION OF THE INVENTION

The inventors have established that an assay based on 2 specific biomarkers:

the plasma level of soluble HLA-G, and the proportion of CD8+ T lymphocytes expressing ILT-2, would provide an accurate, reliable and sensitive method for the prognosis of the outcome of a patient afflicted by a cancer, preferably bladder cancer, or for monitoring the recurrence of a cancer, preferably bladder cancer, in a patient; this is the "second embodiment" as mentioned above.

The inventors have also established that an assay based on the proportion of CD8+ T lymphocytes expressing ILT-2, would provide an accurate, reliable and sensitive method for monitoring the recurrence of a cancer, preferably bladder cancer, in a patient. This is the "first embodiment" as mentioned above.

Definitions Applicable to the Methods According to the First and Second Embodiments CD8+ T lymphocytes are immune T cells which express the CD8 membrane receptor. CD8 is a transmembrane glycoprotein that serves as a co-receptor for the T cell receptor (TCR). CD8 plays an important role in the antigen-immune activation.

HLA-G means Human Leukocyte Antigen G. It refers to an immune-inhibitory protein belonging to the Major Histocompatibility Complex (MHC) class I molecules. HLA-G is a tolerogenic molecule which expression was originally observed and characterized in trophoblasts. It confers protection to the semi-allogeneic foetus from the maternal immune system. HLA-G differs from classical MHC class I molecules by its genetic diversity, expression, structure and functions. It is characterized by a relatively low allelic polymorphism and a highly restricted tissue distribution. HLA-G has membrane-bound and soluble isoforms, and may be monomeric or dimeric.

It has previously been established that HLA-G is expressed by bladder tumor cells (El-Chennawi et al. (2005), The Egyptian journal of immunology/Egyptian Association of Immunologists 12:57-64) and helps tumorous cells to escape to the immune surveillance by host T lymphocytes and natural killer (NK) cells (Paul et al. (1998), Proceedings of the National Academy of Sciences of the United States of America 95:4510-4515). The HLA-G expression by malignant cells may prevent tumor immune eradication by inhibiting the activity of tumor infiltrating NK, cytotoxic T lymphocytes (CTL) and antigen presenting cells (APC).

Plasma level of HLA-G means, according to the invention, plasma concentration of HLA-G.

By ILT-2, it is meant the immunoglobulin-like transcript 2. It is an inhibitory receptor that recognizes HLA-class I among which is HLA-G. It is expressed by some T and NK cells, and by all B and myeloid cells. Cells expressing ILT-2 are inhibited by HLA-G dimers.

As used herein, the patient refers to a mammal, preferably, a human.

Cancer refers to any type of cancer, and may be chosen from bladder cancer, kidney cancer, urogenital cancer and melanoma. Preferably, cancer according to the invention is bladder cancer.

Bladder cancer corresponds to several types of cancer arising from the epithelial lining of the urinary bladder.

The wall of the bladder has 4 main layers:
the innermost lining is made up of cells called urothelial or transitional cells, so this layer is called the urothelium or transitional epithelium;
beneath the urothelium is a thin layer of connective tissue, blood vessels, and nerves, which is called the lamina propria;
next is a thick layer of muscle called the muscularis propria; and
outside of this muscle, a layer of fatty connective tissue separates the bladder from other nearby organs.

Bladder cancer may be invasive or non invasive; preferably, bladder cancer is NMIBC.

Non-muscle invasive cancer or NMIBC refers to forms of bladder cancer in which the disease is confined to the urothelium or the connective tissue and, accordingly, wherein the tumor has not reached the muscle layer of the bladder. According to the American Joint Committee on Cancer TNM staging system for bladder cancer, NMIBC corresponds to tumors classified under the stages:
Ta (non-invasive papillary carcinoma),
CIS (also called Tis, non-invasive flat carcinoma), and
TI (the tumor has grown from the layer of cells lining the bladder into the connective tissue. It has not grown into the muscle layer of the bladder).

Preferably, in the context of the invention, the bladder cancer is non-muscle invasive bladder cancer (NMIBC).

In the context of the present invention, a biological sample refers to any biological sample obtained for the purpose of evaluation in vitro. Typically, said biological sample can be obtained from blood, serum or plasma. Preferably, said biological sample is blood or plasma.

First Embodiment of the Invention

According to said first embodiment, the present invention relates to a method for monitoring the recurrence of a cancer in a patient, comprising a step of measuring the proportion of $CD8^+$ T lymphocytes population expressing ILT-2 within the total population of CD8+T lymphocytes in a biological sample obtained from said patient, wherein when said proportion is high, then the patient is classified as high risk.

Preferably said method is for monitoring the recurrence of a cancer in a patient, wherein when the proportion of $CD8^+$ T lymphocytes population expressing ILT-2 (i.e. "ILT-$2^+$ $CD8^+$ T lymphocytes") within the total population of CD8+T lymphocytes is high, then the patient is classified as high risk; and wherein when the proportion of $CD8^+$ T lymphocytes population expressing ILT-2 within the total population of CD8+T lymphocytes is low, then the patient is classified as non high risk.

Preferably, said method is for monitoring the recurrence of a cancer in a patient, within a year after surgery. Preferably, the cancer is bladder cancer, preferably NMIBC.

Preferably, the measurement of the proportion of $CD8^+$ T lymphocytes population expressing ILT-2 within the total population of CD8+T lymphocytes is measured using all standard techniques in cell detecting/counting methods, and preferably by flow cytometry.

Such a method according to the first embodiment of the invention is quick, sensitive and reliable in the prognosis of the outcome of a patient afflicted by a cancer, preferably bladder cancer, or in monitoring the recurrence of a cancer, preferably bladder cancer, in a patient. Recurrence of a cancer, like bladder cancer, is defined as the return of said cancer after treatment and after a period of time during which said cancer cannot be detected.

This method allows the monitoring of recurrence of a cancer, preferably bladder cancer, in a patient. In such a case, the patient is a patient who was already diagnosed with a cancer, preferably bladder cancer, and who was treated or not yet treated. Preferably, the patient is a patient who was already diagnosed with a cancer, preferably bladder cancer, and who was already treated.

This method also allows the prognosis of the outcome of a patient diagnosed with a cancer, preferably bladder cancer. In such a case, the patient is a patient who is diagnosed with a cancer, preferably bladder cancer.

Such a method according to the first embodiment of the invention presents many advantages: it is reliable, sensitive, quick and easy to perform.

Moreover, the present method is less invasive for the patient and can be carried out in a small amount of time without the necessity to obtain samples from the tumor itself.

According to said first embodiment of the invention, by "high" proportion of ILT-$2^+$ $CD8^+$ T lymphocytes among the total $CD8^+$ T lymphocytes, it is preferably meant a proportion of at least 34%, preferably of at least 35%, preferably of at least 37%, preferably of at least 38%, preferably of at least 39%, preferably of at least 40%, preferably of at least 41%. By "low" proportion of ILT-$2^+$ $CD8^+$ T lymphocytes among the total $CD8^+$ T lymphocytes, it is preferably meant a proportion of less than 33%, preferably of less than 30%.

According to said first embodiment of the invention, by "non high risk" for a given patient, it is meant that said patient will not have an early recurrence of his cancer, preferably no recurrence within a year. By "high risk" for a given patient, it is meant that said patient will have an early recurrence of his cancer, preferably a recurrence within a year.

The classification according to the method of said first embodiment of the invention allows a better identification of patients with high risk of developing a recurrent cancer, preferably a recurrent bladder cancer, and hence a better follow-up of the patients.

Second Embodiment of the Invention

According to said second embodiment, the present invention also relates to a method for the prognosis of the outcome of a patient afflicted by bladder cancer or for monitoring the recurrence of bladder cancer in a patient, wherein said method comprises:
 a) a step of measuring the plasma level of soluble HLA-G in a first biological sample obtained from said patient, and
 b) a step of measuring the proportion of $CD8^+$ T lymphocytes population expressing ILT-2 within the total population of CD8+T lymphocytes in a second biological sample obtained from said patient,
wherein:
 when the proportion measured at step b) is less than 20%, then the patient is classified as non high risk, and
 when the proportion measured at step b) is more than 20% and the plasma level of soluble HLA-G is more than 20 ng/mL, then the patient is classified as high risk.

The method according to said second embodiment of the invention is quick, sensitive and reliable in the prognosis of the outcome of a patient afflicted by a cancer, preferably bladder cancer, or in monitoring the recurrence of a cancer, preferably bladder cancer, in a patient. Recurrence of a cancer, like bladder cancer, is defined as the return of said cancer after treatment and after a period of time during which said cancer cannot be detected.

This method allows the monitoring of recurrence of a cancer, preferably bladder cancer, in a patient. In such a case, the patient is a patient who was already diagnosed with a cancer, preferably bladder cancer, and who was treated or not yet treated.

This method also allows the prognosis of the outcome of a patient diagnosed with a cancer, preferably bladder cancer. In such a case, the patient is a patient who is diagnosed with a cancer, preferably bladder cancer.

The method according to said second embodiment of the invention presents many advantages: it is reliable, sensitive, and quick and easy to perform.

Moreover, the present method is less invasive for the patient and can be carried out in a small amount of time without the necessity to obtain samples from the tumor itself.

According to the method of said second embodiment of the invention, said first and second biological samples may be two different samples, or alternatively said first and second biological sample is a unique (single) sample. Preferably said first and second biological sample is a unique sample. Accordingly, the method of the invention may be performed with a single biological sample of a given patient.

Accordingly, the method according to said second embodiment of the invention is wherein:
 when the proportion measured at step b) is less than 20%, then the patient is classified as non high risk, and
 when the proportion measured at step b) is more than 20% and the plasma level of soluble HLA-G is more than 20 ng/mL, then the patient is classified as high risk.

According to said second embodiment of the invention, by "non high risk" for a given patient, it is meant that said patient will not have an early recurrence of his cancer, preferably no recurrence within a year.

By "high risk" for a given patient, it is meant that said patient will have an early recurrence of his cancer, preferably a recurrence within a year.

The classification according to the method of said second embodiment of the invention allows a better identification of patients with high risk of developing a recurrent cancer, preferably a recurrent bladder cancer, and hence a better follow-up of the patients.

The inventors have also established that the proportion of NKT cells expressing ILT-2 can be used as a third marker in the method according to the second embodiment of the invention for the prognosis of the outcome of a patient afflicted by a cancer, preferably bladder cancer, or for monitoring the recurrence of a cancer, preferably bladder cancer, in a patient. All the technical features disclosed above are applicable here.

Accordingly, the invention further relates to the method described herein further (second embodiment) comprising a step c) of measuring the proportion of NKT cells population expressing ILT-2 within the total population of NKT cells in a third biological sample obtained from said patient. When the proportion measured at step c) is more than 45%, then the patient is classified as high risk.

Natural killer T cells or NKT cells refers to cells of the immune system. NKT cells share immunological properties of both natural killer cells and T cells. They recognise the antigens carried by the antigen-presenting proteins. They induce immunological reactions by the production of several cytokines and chemokines.

Preferably, said third biological sample is different from the first and second biological samples. Preferably, alternatively, it is the same biological sample as said first or second biological sample. Preferably, alternatively, the first, the second and the third biological sample is a unique sample.

The method according to the second embodiment of the invention may be carried out by several means.

Step a) can be performed by using standard immunodiagnostic techniques, including immunoassays such as competition, direct reaction, or sandwich type assays. Non-limiting examples of methods for measuring the plasma level of soluble HLA-G include, but are not limited to, agglutination tests; enzyme-labelled and mediated immunoassays, such as ELISAs; biotin/avidin type assays; radioimmunoassays; immunoelectrophoresis; immunoprecipitation; and Luminex assays. It falls within the ability of the person skilled in the art to carry out such methods. The reactions generally include revealing labels such as fluorescent, chemiluminescent, radioactive, enzymatic labels or dye molecules, or other methods for detecting the formation of a complex between the antigen and the antibody or antibodies reacted therewith. Preferably, the plasma level of HLA-G is measured by immunoassay.

Step b) may be performed using all standard techniques in cell detecting/counting methods. Preferably, step b) is performed by flow cytometry.

The invention further relates to a kit, said kid comprising:
 means for measuring soluble HLA-G in a biological sample, preferably a plasma sample; and
 means for detecting the presence of CD8+T lymphocytes expressing ILT-2 in a biological sample.

Said kit is preferably used for prognosing the outcome of a cancer, or for monitoring the recurrence of a cancer, preferably bladder cancer.

All the technical features disclosed above are applicable.

As previously mentioned, the inventors found out that high plasma level of soluble HLA-G in combination with a high proportion of ILT-2 expressed by CD8+T lymphocytes is associated with a high risk of recurrence of bladder cancer in a patient.

The inventors have established that bladder cancer may be treated by inhibiting HLA-G.

Accordingly, a further embodiment of the invention relates to an anti HLA-G antibody for use for treating a cancer in which tumor cells express HLA-G (i.e. are HLA-G positive). Accordingly, a further embodiment of the invention relates to an anti HLA-G antibody for use for treating bladder cancer, particularly NMIBC.

In the context of the invention, treating or treatment means reversing, alleviating, inhibiting the progress of, or preventing bladder cancer, or reversing, alleviating, inhibiting the progress of, or preventing one or more symptoms of bladder cancer.

Said treatment may be particularly useful for treating patients classified as high risk according to the method of the present invention.

Typically, said anti-HLA-G antibody is chosen among polyclonal antibody, monoclonal antibody, chimeric antibody, humanized antibody, antibody fragments and antibody derivatives. The anti-HLA-G antibody is preferably a monoclonal antibody.

Anti HLA-G antibodies can be administered by any suitable route of administration. Examples of routes of administrations are topical, oral, parenteral, intranasal, intravenous, intramuscular, subcutaneous or intraocular administration and the like. Preferably, the anti HLA-G antibodies are administered by intravesical instillation.

Finally, the invention also relates to a method for treating a cancer (preferably bladder cancer, preferably NMIBC) in a patient, comprising:
 a step of measuring the proportion of CD8$^+$ T lymphocytes population expressing ILT-2 within the total population of CD8+T lymphocytes in a biological sample obtained from said patient, wherein when said proportion is high, then the patient is classified as high risk, and
 a step of treating the patient classified as high risk with an appropriate therapy.

The definitions of the first embodiment here apply.

Finally, the invention also relates to a method for treating a cancer (preferably bladder cancer, preferably NMIBC) in a patient, comprising:
 a) a step of measuring the plasma level of soluble HLA-G in a first biological sample obtained from said patient, and
 b) a step of measuring the proportion of CD8$^+$ T lymphocytes population expressing ILT-2 within the total population of CD8+T lymphocytes in a second biological sample obtained from said patient,
wherein:
 when the proportion measured at step b) is less than 20%, then the patient is classified as non high risk, and
 when the proportion measured at step b) is more than 20% and the plasma level of soluble HLA-G is more than 20 ng/mL, then the patient is classified as high risk; and
 a step of treating the patient classified as high risk with an appropriate therapy.

The definitions of the second embodiment here apply.

Such a therapy may be chosen from surgery (transurethral resection (TUR)), chemotherapeutic agents and BCG.

The present invention will be better understood in view of the following examples and figures, which are not limitative.

Example 1: Relevancy of sHLA-G Expression and ILT-2 Expression on CD8+ T Cells in NMIBC Material and Methods Patients and Samples NMIBC patients were prospectively followed in the Urology Unit of the Saint Louis Hospital (Paris, France) from August 2013 to September 2014. Patients who fulfilled the following criteria were enrolled in this prospective longitudinal study: i) no under immunomodulator concomitant medication; ii) free of acute or chronic infectious diseases; iii) currently free of other tumors; iv) no previous or current tumor-based radiotherapy; v) no autoimmune disease.

Antibodies

The following antibodies were used in this study:
 from Orthoclone, anti-CD3 clone OKT3;
 from ebioscience, anti-CD3-PerCPCy5.5, -CD3-eFluor450, -CD4-PerCPCy5.5, -CD8-FITCCD14-PerCPCy5.5, -CD19-PerCPCy5.5, CD25-Alexa488, -CD56-FITC, -CD68-FITC, -CD163-APC, -CD206-eFluor450, -IFNG-PE-Cy5.5; -TCR gamma/delta-FITC;
 from Exbio Praha, anti-HLA-G clone G233;
 from Dako, polyclonal anti-human-B2M;
 from Beckman Coulter, anti-ILT2-PE clone HP-F1;
 from Biolegend, anti-ILT2 clone GH 75;
 from Santa Cruz, anti-HLA-G clone 4H84;
 from Beckman-Coulter, goat anti-mouse FITC.

Immunohistochemistry

Immunohistochemistry analyses on paraffin-embedded tissue slides of bladder cancer tumors were performed according to the previously published method (Creput et al, J Hepathol, 2003) using the 4H84 antibody.

Phenotyping

For ILT2 and ILT4 expression studies on PBMC lymphocyte subsets, peripheral blood mononuclear cells from healthy donors and bladder cancer patients were incubated with the following antibody combinations: CD8-FITC/ILT2-PE/CD4-PerCPCy5.5/CD3-APC (T cells), CD56-FITC/ILT2-PE/CD3-PerCPCy5.5 (NKT cells), ILT2-PE/CD19-PerCPCy5.5 (B cells), TCRg/d-FITC/ILT2-PE (gamma/delta T cells), CD68-FITC/ILT2-PE/CD14-PerCPCy5.5/CD163-APC/CD206-eFluor450 (M2 monocytes).

For ILT4 expression on these subsets, anti-ILT4-PE antibody was substituted to anti-ILT2-PE.

Soluble HLA-G measurement in plasma

The sHLA-G quantification was performed in 100 µl EDTA plasma as described in Rebmann et al. ((2007), Human immunology, 68: 251-258)) except that Bioplex beads (Bio-Rad) and the anti-HLA-G antibody G233 (Exbio, Praha) were used, and that analysis was performed on a BD Canto II cytometer. Standard reagent was culture supernatant of cells transfected with the B2M-HLA-G5 fusion protein (Favier et al. (2011), PloS one, 6:e21011) calibrated using a purified HLA-G5 protein (Rebmann et al. (2007), Tissue antigens, 69 Suppl 1: 143-149).

Capture of Naturally Produced HLA-G from NMIBC Patients' Plasma

HLA-G molecules present in plasma from NMIBC patients were captured as in Le Rond et al. ((2006), J Immunol, 176: 3266-3276) using magnetic beads coated with goat anti-mouse IgG Ab (Ademtech). Beads were incubated overnight at 4° C. with anti-HLA-G, G233 mAb, and after three washing steps, G233-coated beads were incubated with plasma from NMIBC patients, or healthy controls (14.108 beads for 300 µl of plasma). After extensive washes, beads were collected by magnetic separation and then used in functional assays.

Functional Assays

PBMC from healthy donor controls or NMIBC patients were stimulated using anti-CD3 or PMA/ionomycin. For T cell activation using anti-CD3, PBMC were thawed and stimulated for 24 hours by 50 ng/ml anti-CD3 (OKT3, orthoclone) in the presence or absence of 5 μg/ml recombinant HLA-G and/or 10 μg/ml anti-ILT2 antibody GH 75 (BD Pharmingen). CD25 up-regulation was then assessed on CD4+ and CD8+ lymphocytes by flow cytometry. For T cell activation using PMA/ionomycin, PBMC were thawed and stimulated for 4 hours by 50 μM PMA (SIGMA) and 500 ng/ml ionomycin (Sigma) in the presence or absence of 5 μg/ml recombinant HLA-G and/or 10 μg/ml anti-ILT2 antibody GH 75 (Biolegend). Golgi-Stop reagent (Life Technologies) was systematically added from the start of the stimulation as recommended by the provider. IFNG production by CD4+ and CD8+T lymphocytes was then then assessed by flow cytometry.

Statistical Analyses

Qualitative variables were expressed as number of cases (percentage), meanwhile continues variables were expressed as mean (standard deviation).

For the purpose of the analysis, patients were grouped based on the tumor recurrence risk applying the European Organisation for Research and Treatment of Cancer (EORTC) score. Thus, patients were classified as Low Risk (EORTC score=0), Intermediate Risk (EORTC score between 1 and 9) or High Risk (EORTC score>10). The bivariate analysis of the immunological parameter was performed using Students t Test or Welch test (according variances equality) in the case that group encompassed more than 30 patients, or Mann-Whitney U test in the case that groups encompass less than 30 patients. The variances equality was examined using the Levene test, while the normality distribution will be examined using the Shapiro test. Meanwhile, frequencies' bivariate analysis was performed using Chi-Square test or Fisher exact test when the expected values in any of the cells of a contingency table are below 5%. For the analysis of more than 2 categories the analysis was performed using Kruskall-Waillis test or one-way ANOVA test, basis on the distribution of the values and the number of patients included in each group.

The likelihood of experience a tumor relapse based on immunological parameters was evaluated. Predictive accuracy was assessed by comparing the area under the receiver operating characteristic (AUROC) curves. Those immunological parameters identified as potential predictive variables were selected to develop a prognostic clinical tool. The positive predictive value (PPV) and negative predictive value (NPV) were defined as the probability to have or not a tumor relapse based on the expression of the identified immunological parameters, respectively, expressed with two-side 95% confidence interval (95% CI), calculated using the exact binomial distribution.

Analyses were carried out using the SPSS statistical software package version 18.0 (IBM Corporation, Somers, N.Y., USA) and GraphPad Prism version 6 (San Diego, Calif., USA).

Results

Forty-nine patients were included in the study. Seven (14.2%) patients were classified as High-Risk (HR), 42 (85.8%) patients as Intermediate Risk, and none as Low Risk for recurrence. As control group, forty-eight healthy donors were enrolled from the French Blood Bank.

HLA-G Expression by Bladder Tumors

Figure 1:
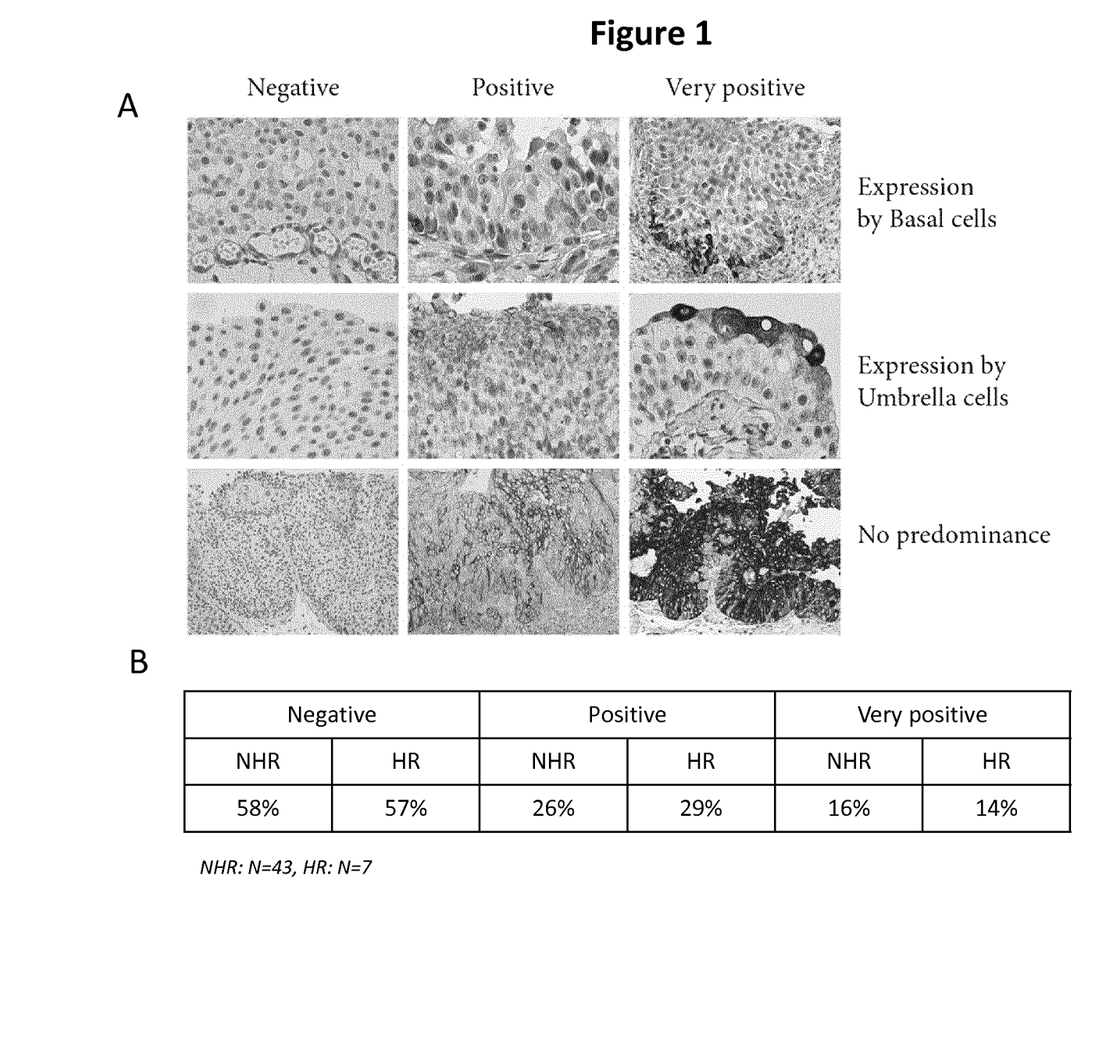
FIG. 1: HLA-G Expression by Non-High-Risk (NHR) and High-Risk (HR) Tumors

In previous studies, HLA-G expression by tumor cells and soluble HLA-G levels were evaluated, but no correlation between these parameters and clinical status was found [El-Chennawi et al. (2005), The Egyptian journal of immunology/Egyptian Association of Immunologists 12:57-64, and Gan et al. (2010), Human immunology, 71:899-904]. The present study focused on low grade tumors not infiltrating the muscle (NMIBC) and on their risk of recurrence according to the EORTC recommended classification. Thus, patients were sorted according to these criteria into non-high risk (NHR) and high risk (HR) groups and HLA-G expression by the tumors was evaluated by immunohistochemistry. HLA-G expression in tumors could be detected in basal cells, superficial cells, or in both, with variable intensities defining three subgroups: HLA-G negative, positive, and very positive. Representative results are shown in FIG. 1A. However, no differences were seen between NHR and HR patients: HLA-G negative, positive, and very positive subgroups represented the exact same proportions of tumors from both NHR and HR patients (FIG. 1B).

Soluble HLA-G Plasma Levels

Figure 2:
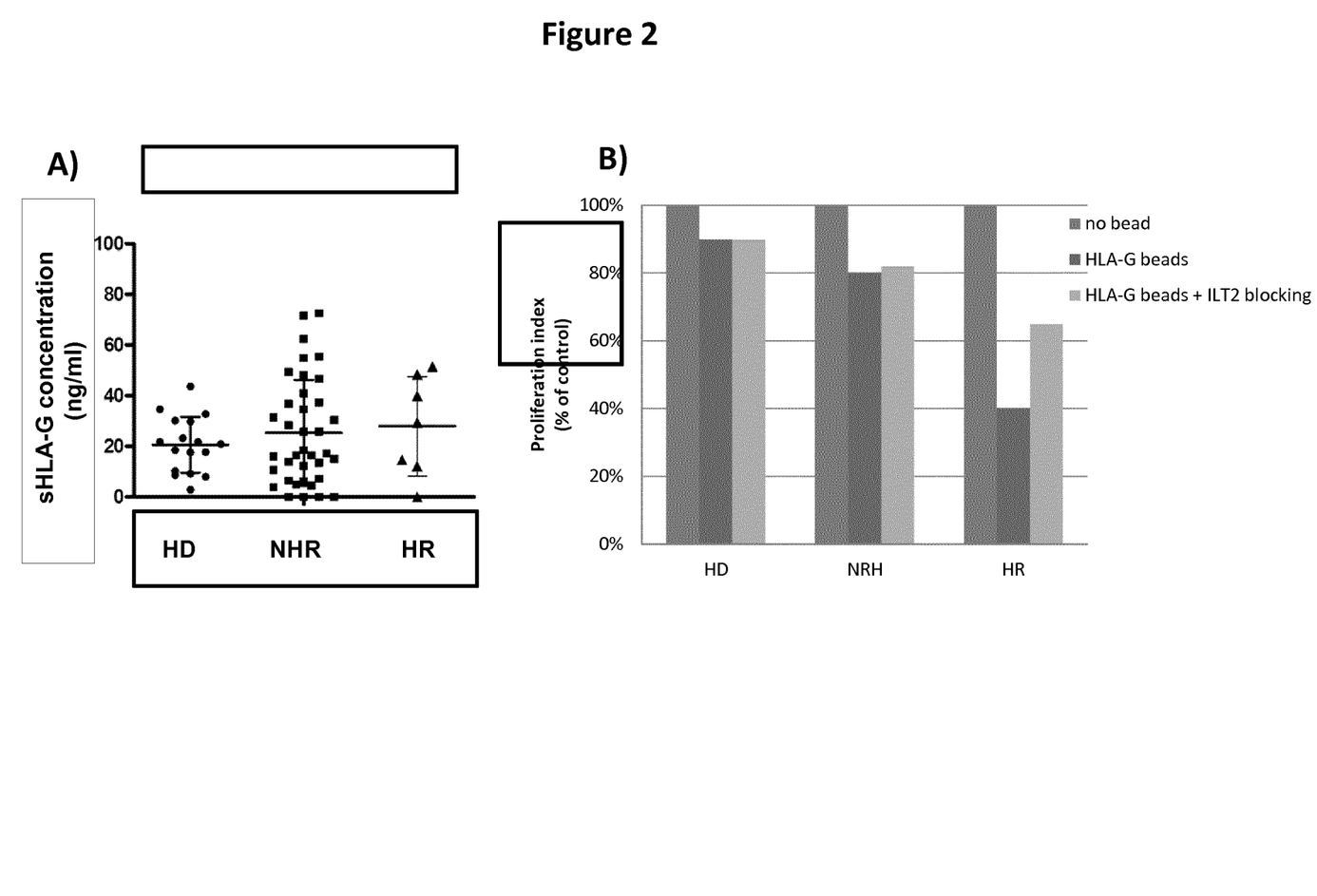
FIG. 2: sHLA-G Expression by Healthy Donors (HD), Non-High-Risk (NHR) and High-Risk (HR) Tumors FIG. 2A) is a graph showing soluble HLA-G plasma levels of healthy donors (HD), non-high risk (NHR) and High risk (HR) of recurrence patients. sHLA-G concentrations were obtained using luminex methodology as described in the Materials and Methods section. HD: N=17, NHR: N=47, HR: N=7.

The inventors next investigated soluble HLA-G plasma levels in healthy donors (HD) and NMIBC patients. Their analysis, conducted on 49 patients, revealed no statistically significant differences between HD and bladder cancer patients (22.2 ng/ml±10-1 ng/mL vs. 25.7 ng/ml±20.5 ng/mL, p=0.509), which is in line with previous reports (Gan et al. (2010), Human immunology, 71:899-904). However, whereas both HD and NHR patients had similar soluble HLA-G plasma levels (22.2 ng/ml±10-1 ng/mL vs. 25.2 ng/ml±20.9 ng/mL, p=0.571), soluble HLA-G plasma levels from all 7 HR patients were higher, but without statistically significant, than levels from both HD patients (27.9 ng/ml±19.6 ng/mL) (FIG. 2A).

The inventors next sought to determine whether HLA-G molecules that made up for increased soluble HLA-G plasma levels had a chance of contributing to anti-tumor immune response inhibition. The inventors first performed immuno-precipitation experiments followed by western blotting on plasma HLA-G in order to evaluate whether it was under inactive monomeric or active dimeric forms. Their results show that plasma HLA-G from HR patients is made up of 60% dimers, whereas that from NHR patients contains only 30% dimers, and that from HD was undetectable. Thus, in HR patients, increased soluble HLA-G concentrations were associated with an increased proportion of dimeric, potentially active HLA-G.

The inventors next verified that soluble HLA-G from HR patients was indeed active. For this, they captured plasma HLA-G on nanobeads, and evaluated their capability to inhibit anti-CD3-mediated T cell polyclonal activation. As shown in FIG. 2B, beads coated with HLA-G from HR plasma (HR HLA-G beads) inhibited T cell proliferation by 60%, whereas HD and NHR HLA-G beads had no effect. The inhibitory effect of HLA-G-coated beads was partially prevented by addition of a blocking anti-ILT2 antibody, indicating that inhibition was due to the HLA-G/ILT2 interaction. Thus, these data demonstrated that active soluble HLA-G molecules are specifically increased in the plasma of HR patients.

HLA-G Receptor Cell-Surface Expression on Immune Cell Subsets

The inventors next investigated if in HR patients, immune cell subpopulations capable of being inhibited by HLA-G, i.e. ILT2- and/or ILT4-expressing cells, were over-represented. Systematic phenotyping for ILT2 and ILT4 cell-surface expression was therefore performed on PBMC from all patients and concomitantly processed HD, on CD4+ and CD8+ T cells, NK cells, NKT cells, B cells, monocytes. ILT2 and ILT4 expression by Tγ/δ cells and CD206+ CD163+M2 macrophages were also investigated, albeit not systematically.

Figure 3:
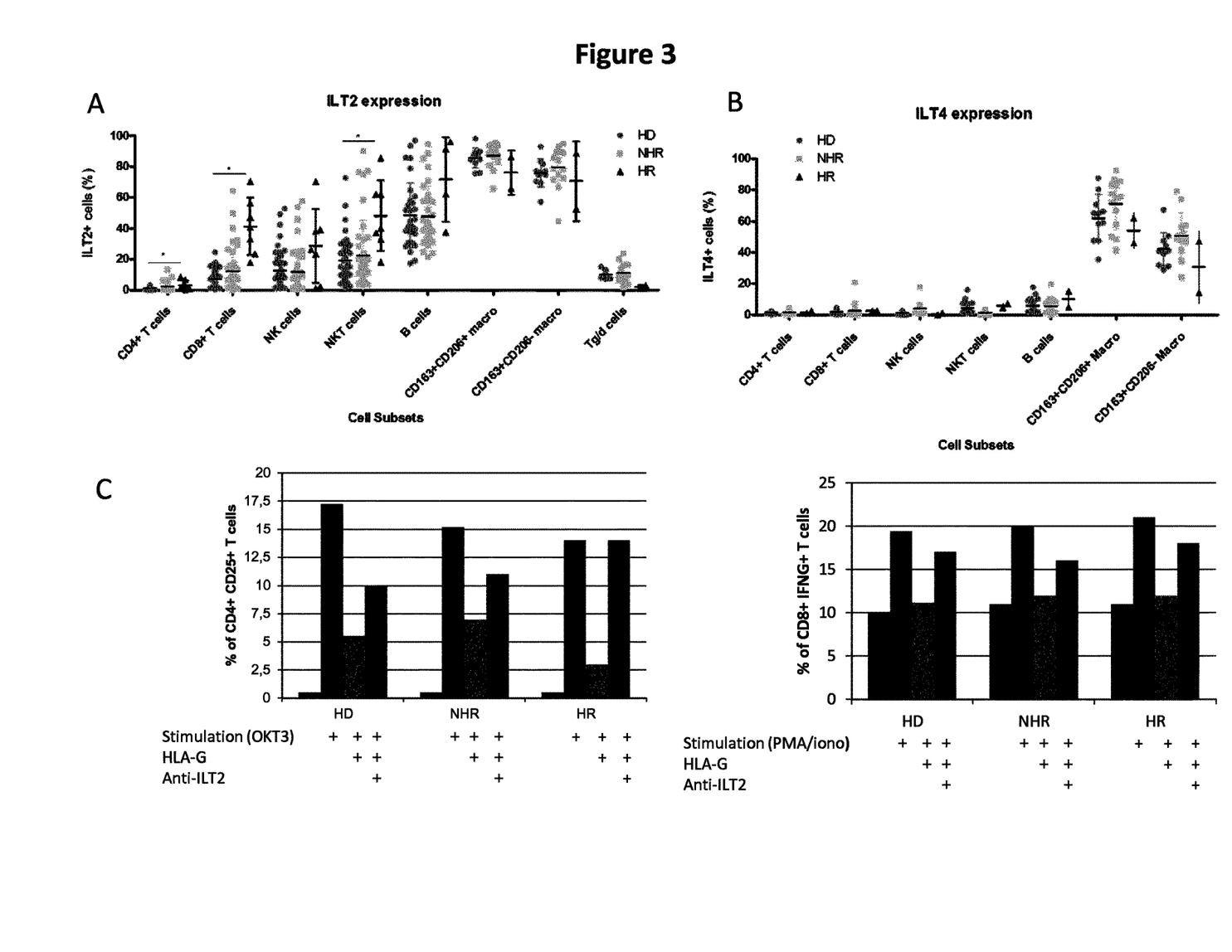
FIG. 3: HLA-G Receptor Expression by Healthy Donors (HD), Non-High-Risk (NHR) and High-Risk (HR) Tumors FIG. 3A) is a graph showing ILT2 expression by PBMC immune cell subsets from healthy donors (HD), non high risk (NHR) and high risk (HR) patients. CD4: CD3+CD4+ T cells. CD8: CD3+CD8+ T cells. NK: CD3-CD56+NK cells. NKT: CD3+CD56+ NKT cells. B: B cells. GD: gamma/delta T cells. Results are presented as percentages of ILT2-expressing cells within the indicated cell subset.
Figure 4:
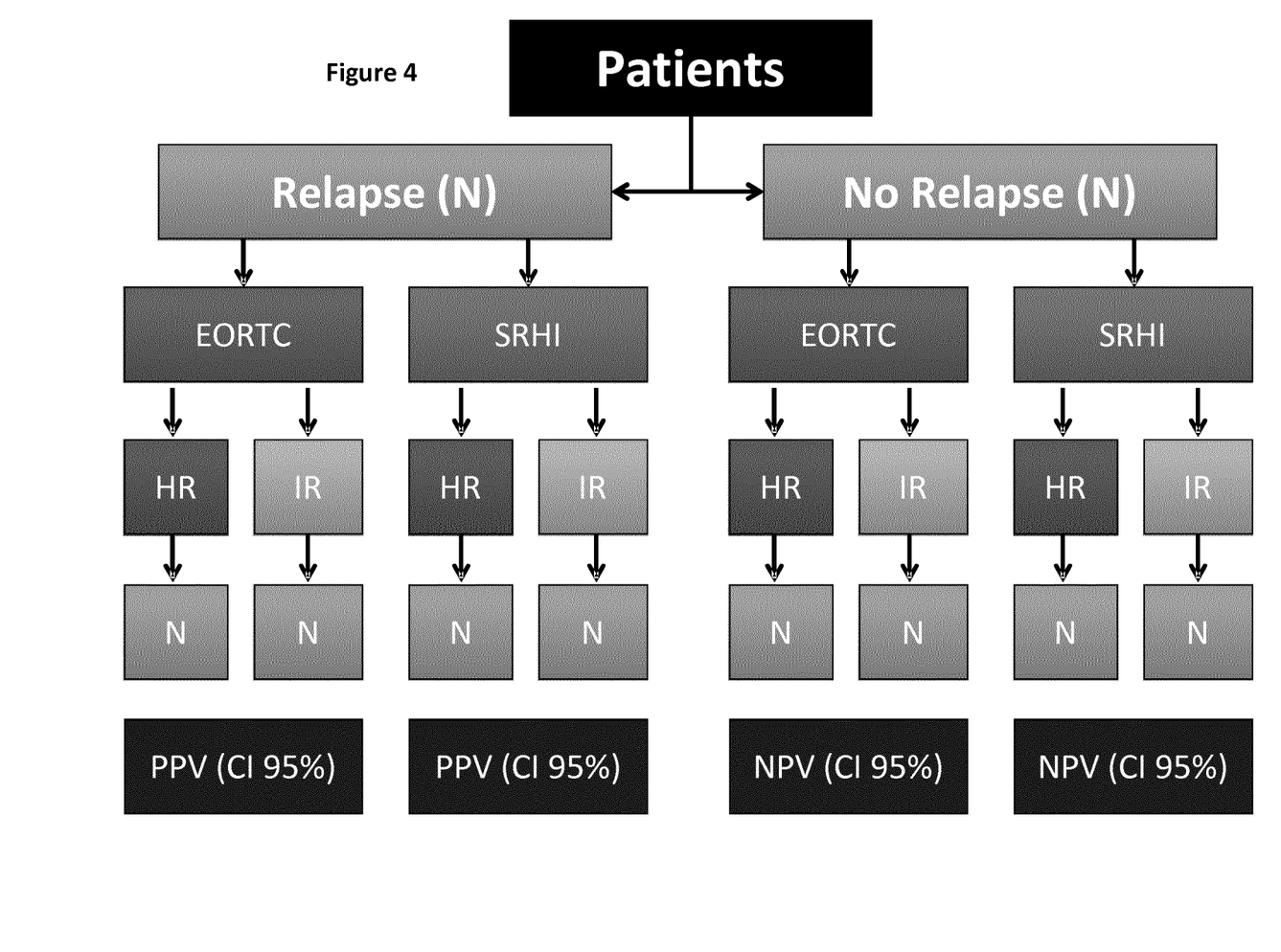

The obtained results are presented in FIG. 3A for ILT2 and FIG. 3B for ILT4. No differences were found regarding ILT4-expressing subpopulations between HD, NHR, and HR patients. However, analysis of ILT2-expressing populations revealed that this HLA-G receptor was indeed differentially expressed by the cellular populations investigated. In HD, the ILT2-expressing populations represented an average of 1.01% of CD4+ T cells, 7.14% of CD8+ T cells, 13.6% of NK cells, 19.1% of NKT cells, and 50% of B cells, and 100% of monocytes. These values are similar to what has been published by others [Colonna et al. (1997), The Journal of experimental medicine, 186: 1809-1818, and Naji et al. (2014), J Immunol, 192: 1536-1546.]. In PBMC from bladder cancer patients, ILT2 expression was significantly increased in CD4+ T cells (2.48%, $p<0.001$), CD8+ T cells (16.4%, $p<0.001$), NKT cells (26.3%, $p=0.038$), and NK cells (68%, $p<0.001$), but not in Tγ/δ cells or B cells. The inventors then compared HD, NHR and HR subgroups. They found that ILT2 expression was significantly higher in NHR than in HD for CD4 T cells (2.38%, $p=0.004$) and CD 8 T cells (17.2%, $p=0.039$). These differences in ILT2 expression were even more striking in HR patients, for whom, ILT2-expressing cells represented 3.09% of CD4+ T cells ($p=0.133$), 41.2% of CD8+ T cells ($p<0.001$), 28.6% of NK cells ($p=0.183$), and 48.2% of NKT cells ($p<0.001$). Comparison between HR and NHR patients showed differences in CD8 T cells ($p<0.001$) and NKT cells ($p=0.004$), but not in CD4 T cells ($p=0.0775$) or NK cells ($p=0.117$). Thus, these data demonstrated that in addition to active plasma HLA-G, as seen before, cytotoxic immune effector cell populations potentially capable of being inhibited by HLA-G were increased in HR patients. The inventors next investigated if these effector cell populations were still functional and sensitive to inhibition by HLA-G.

The inventors investigated the capability of the ILT2-expressing cells and their ILT2-negative counterparts to (i) upregulate CD25 in response to anti-CD3 polyclonal stimulation, or to produce IFNG in response to PMA/ionomycin stimulation, and (ii) be inhibited by soluble HLA-G. FIG. 3C shows that CD4+ and CD8+ T cells from HD, NHR and HR patients responded equally well to stimulation by either anti-CD3 or PMA/ionomycin stimulation. This indicated that the capability of effector cells from NHR and HR bladder cancer patients to respond to immune stimulation was not impaired and that these cells were not anergic. FIG. 3C also shows that both CD25 upregulation by CD4+ T cells after OKT3 stimulation, and IFNG production upregulation by CD8+ T cells after PMA/ionomycin stimulation were inhibited by HLA-G to a similar extent for HD, NHR, and HR patients. This inhibition was partially prevented if the HLA-G-ILT2 interaction was blocked. This demonstrates that effector cells from all three groups were still sensitive to HLA-G-mediated inhibition through ILT2 engagement. This also indicates that the expansion of ILT2-expressing cell populations in NHR and even more so in HR patients corresponds to an increase in the HLA-G-sensitive immune effector cell population.

Taken together, these data demonstrate that in HR patients, plasma concentrations of active HLA-G, and the proportions of ILT2-expressing CD8+ T cells and NK cells that may be inhibited by it both significantly increased. The inventors next evaluated if these parameters could be used to characterize HR patients.

HR Patient's Immunological Profile

Based on the analyses performed, the inventors selected ILT2 expression on CD8+ T cells and NKT cells as potential markers associated with high risk of recurrence (HR patients). They first found that HR patients exhibit a positive, but not statistically significant correlation between ILT2 expression levels in CD8 T cells ($r=0.502$, $p=0.38$) and NKT cells ($r=0.48$, $p=0.4$) and the plasma soluble HLA-G concentrations. Interestingly, when this analysis was performed for the NHR population, this correlation seemed to be negative ($r=-0.49$, $p=0.01$ for CD8+ T cells and $r=-0.38$, $p=0.06$ for NKT cells). This finding suggests that in the development of a predictive tool, the single consideration of ILT2 expression without plasma soluble HLA-G quantification would misclassify NHR patients.

Secondly, the inventors analysed the predictive accuracy of ILT2 expression by CD8 T cells and NKT cells, and plasma soluble HLA-G using AUROC. The best AUROC value was obtained for CD8+ T cell ILT2 expression levels (0.95, 95% CI: 0.88-0.99; $p<0.001$). The cut-off value identified was of 20% of CD8+ T cells expressing ILT2.

The proportion of NKT cells expressing ILT2 yielded an AUROC value of 0.82 (95% CI: 0.67-0.97; $p=0.02$), identifying a cut-off value of 45%. Plasma soluble HLA-G had an insufficient predictive accuracy (0.41; 95% CI: 0.37-0.86) with a cut-off value of 20 ng/mL. Nevertheless as the inventors have shown above, the predictive value of soluble HLA-G could vary according to patient population.

The inventors then classified the studied population applying two parameters: first ILT2 expression on CD8+ T cells, and second, plasma soluble HLA-G concentrations using the cut-offs identified by AUROC. Thirty-five (71.4%) patients showed an ILT2 expression on CD8 T cells lower than 20%. Out of these, all but one (97.1%) were NHR according to EORTC classification. Among the 14 (28.6%) patients with an expression ILT2 expression on CD8+ T cells higher than 20%, 7 patients had plasma soluble HLA-G concentrations higher than 20 ng/ml. Among these 7 patients bearing both unfavourable immunological markers, 4 (57.1%) were HR according to EORTC classification. Of the 7 patients showing higher expression of ILT2 on CD8+ T cells but low levels of soluble HLA-G, 5 (71.4%) were NHR according to EORTC classification. This discordance between the immunological classification and the EORTC classification was investigated during the follow-up.

Risk of Relapse at 1 Year

Classification of the risk of relapse to the immunological profile was constructed as follows: SRHI_LowRisk (SRHI-LR): <20% CD8+ T cells expressing ILT2.

SRHI_IntermediateRisk (SRHI-IT): >20% of CD8+ T cells expressing ILT2 and plasma soluble HLA-G concentration<20 ng/mL. SRHI_HighRisk (SRHI-HR)>20% CD8+ T cells expressing ILT2 and plasma soluble HLA-G concentration>20 ng/mL. Accordingly, 7 patients out of 49 studied were SRHI-HR (4 EORTC-HR), 7 SRHI-IR (2 EORTC-HR), and 35 SRHI-LR (1 EORTC-HR).

At the moment of the analysis 20 patients have completed at least 1 follow-up at 6 months after baseline visit. Seven (35%) experienced tumor relapse. Of them, 4 were SRHI patients and 3 EORTC HR. None of the 3 EORTC HR patients who experienced relapse were discordant with the SRHI HR classification. This data suggests that immunological combination could have a higher predictive value for tumor relapse than the EORTC classification.

Among the 13 patients free of relapse, 1 was classified as HR according to EORTC and 1 according to SRHI classifications. This data suggests that immunological combination could have a similar number of HR misclassified patients to the EORTC classification.

Example 2: ILT2 Expression on Peripheral CD8+ T Cells is a Recurrence Prognosis Marker in NMIBC The inventors designed a prospective longitudinal study including patients diagnosed with NMIBC. Inclusion criteria were: i) no under immunomodulator concomitant medication; ii) free of acute or chronic infectious diseases; iii) free of other tumors; iv) no previous or current tumor-based radiotherapy or chemotherapy; v) no autoimmune disease. All patients gave their informed consent to this study, which was approved by the local institutional board.

Healthy blood donors from the blood donors unit of the St Louis Hospital were systematically included. For all these patients, samples were collected on the day of surgery. Tumor HLA-G expression was evaluated by immunohistochemistry on resection biopsies using the 4H84 antibody (Menier C, Saez B, Horejsi V, Martinozzi S, Krawice-Radanne I, Bruel S, Le Danff C, Reboul MHilgert I, Rabreau M, et al. (2003). Characterization of monoclonal antibodies recognizing HLA-G or HLA-E: new tools to analyze the expression of nonclassical HLA class I molecules *Human immunology* 64, 315-326), plasma HLA-G was measured by Luminex (Rebmann V, Switala M, Eue I, Grosse-Wilde H (2010). Soluble HLA-G is an independent factor for the prediction of pregnancy outcome after ART: a German multi-centre study *Hum Reprod* 25, 1691-1698), and ILT2 cell-surface expression was measured on peripheral blood mononuclear cell subsets by flow cytometry using the anti-ILT2 HP-F1 clone in combination with immune lineage markers. Acquisition was performed on a BD CANTO II and analysis was done using the FlowJo Software. Patients were then followed according to routine procedures, with trimestrial flexible cystoscopy.

One year after initial surgery (12+/−1 month, to accommodate according clinical practice constraints), patients were segregated into "recurring" if tumor recurrence had occurred, and "non-recurring" if no tumor was found by cystoscopy. The end-point of the study was the development of tumor recurrence.

Continuous variables are expressed as medians and quartiles (Q1-Q3) and were analyzed using the Mann-Whitney U test. Categorical variables are expressed as numbers of cases and percentages. Predictive accuracy of immunological parameters was assessed by comparing the area under the receiver operating characteristic (AUROC) curves. The baseline time-point was considered the patient recruitment date (value of 0). The time-to-event was computed as the number of months from recruitment date to tumor recurrence. Censored time was defined as time-to-event. Survival curves were plotted using the Kaplan-Meier method, and survival rates and life tables were compared using the log-rank test. Statistical analyzes were performed using the SPSS statistical software (IBM Corporation, USA) and GraphPad Prism (GraphPad Software, USA). All statistical tests were two-sided, and a P value of less than 0.05 was considered statistically significant.

Figure 5:
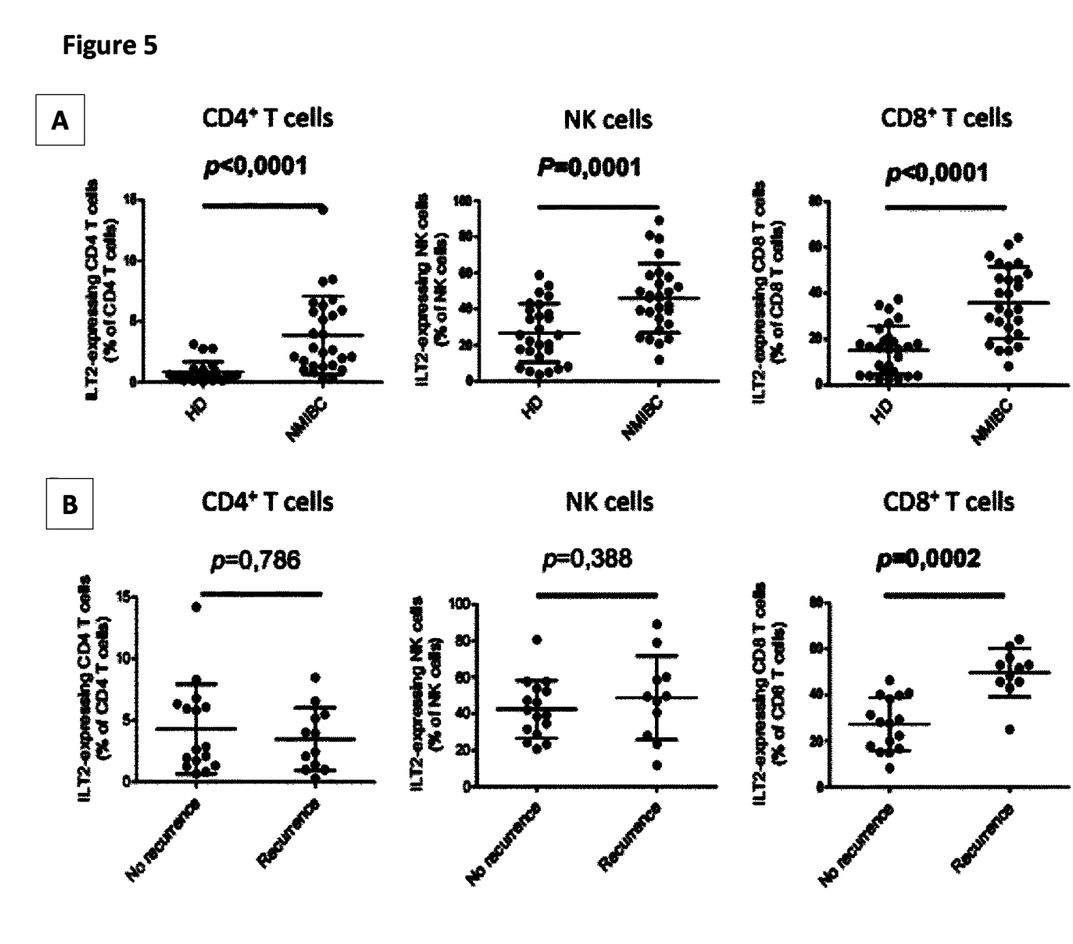
FIG. 5A) is a graph illustrating ILT2 expression levels on peripheral CD3+CD4+ T cells, CD3+CD8+ T cells and CD3-CD56+NK cells for 25 healthy donors (HD) and 27 NMIBC patients. Mean and standard derivation are shown. P was calculated using Mann-Whitney test.
FIG. 5B) is a graph illustrating ILT2 expression levels on peripheral CD3+CD4+ T cells, CD3+CD8+ T cells and CD3-CD56+NK cells from 14 recurring and 13 non-recurring NMIBC patients. Mean and standard deviation are shown. P was calculated using Mann-Whitney test.

Twenty-seven patients matched the inclusion criteria and constituted the study population. Twenty five healthy donors were included. The majority of patients were male (23; 85.2%), aged a median of 68 years (12), and 13 patients (76.5%) were smokers. According to tumor infiltration, 19 patients were pTa (70.4%), 2 were pTis (7.4%), and 6 were pT1 (22.2%). The tumor grade was G2 in 18 patients (72%), and G3 in 7 patients (28%); there was no G1 tumor. Out of the 27 patients, 11 recurred (40.7%), and 16 did not (59.3%). Immunohistochemistry analyzes on tumor biopsies revealed HLA-G expression in 11 out of 27 patients (40.7%) (data not shown). No association between HLA-G expression and recurrence was found (p=0.721), as previously reported (El-Chennawi F A, Auf F A, El-Diasty A M, El-Daim M A, El-Sherbiny S M, Ali A, El-Baz M, El Hameed M A, Paul P, Ibrahim E C, et al. (2005). Expression of HLA-G in cancer bladder *The Egyptian journal of immunology/Egyptian Association of Immunologists* 12, 57-64). Similarly, no differences in soluble plasma HLA-G levels were found between NMIBC recurrence and non-recurrence patients, as expected (p=0.950, data not shown) (Gan L H, Huang L F, Zhang X, Lin A, Xu D P, Wang Q, Wang T J, Yan W H (2010). Tumor-specific upregulation of human leukocyte antigen-G expression in bladder transitional cell carcinoma Human immunology 71, 899-904). Flow cytometry analyzes on peripheral immune subsets revealed that ILT2 expression was increased in NMIBC patients compared to healthy donors on CD4+ T cells (3.7%+/−2.9 vs 0.8%+/−0.8, p<0.0001), CD8+ T cells (34.5%+/−17.8 vs 15.3%+/−10.4, p<0.0001), and NK cells (50.3%+/−19.5 vs 26.6%+/−16.1, p<0.0001) (FIG. 5A). Among NMIBC patients, recurring patients showed similar levels of ILT2 expression on CD4 T cells (p=0.786) and NK cells (p=0.388) to non-recurring patients. However, a strong association was found between recurrence and high ILT2 expression on CD8+ T cells (46.5%+/−11.5% vs 24.7%+/11.0%, p=0.0002) (FIG. 5B).

In order to assess whether the proportion of the CD 8+ ILT2 subpopulation at the time of surgery could be used as a simple test to predict NMIBC recurrence within the next year, the percentage of CD8+ T cells expressing ILT2 was correlated with recurrence-free survival time using ROC curve analysis. The area under the curve for this analysis was of 0.841 (CI 95%: 0.650-0.952), and the best separation of the curves achieved a cut-off level of 41% of CD8+ T cells expressing ILT2. Using this value, a sensitivity of 0.820 and a specificity of 0.875 for predicting tumor recurrence at 1 year were obtained, corresponding to a positive predictive value PPV=0.820 and a negative predictive value NPV=0.880. Kaplan-Meier recurrence-free survival analyzes according to CD8+ ILT2+ score (using 41% as cut-off value) were made. At six months, 93.8% of patients expressing less than 41% of CD8ILT2+ remain recurrence-free compared with 54.5% of patients expressing more than 41% of CD8ILT2+. At 1 year, 9 out of 11 patients (81.8%) with more than 41% of peripheral CD8 T cells expressing ILT2 experienced recurrence within a year, whereas in patients with less than 41% CD8+ ILT2+T only 2 out of 16 recurred (p=0.0001, Log Rank test).

The median time-to event in patients expressing more than 41% of CD8+ ILT2+ was 8.1 months (95% CI: 5.56-10.7 months), compared with 14.1 months (95% CI: 12.6-15.5 months) in patients with a CD8+ ILT2+ expression lower than 41%. This difference implies a Hazard Ratio of 10.1 (95% CI: 2.836.3).

The nature of the augmented ILT2-expressing CD8+ T cell population in NMIBC patients is currently being investigated, and the mechanism that leads to ILT2 over-expression in CD8+ T cells is unknown. However, since ILT2 is an inhibitory receptor that can bind HLA Class I molecules, including the immune checkpoint molecule HLA-G, one can hypothesize that CD8+ T cells expressing high ILT2 levels are constitutively inhibited T cells and of low reactivity.

Because they can represent a very large proportion of CD8+ T cells (up to 70% in the studied cohort), it is very conceivable that in such patients, the overall immune reactivity of the CD8+ T cell compartment, responsible for anti-tumor immunity in bladder cancer, is weakened, leading to decreased tumor control and therefore to tumor accelerated regrowth, i.e. recurrence.

In conclusion, this study demonstrates that a high proportion of peripheral CD8+ T cells expressing ILT2 is strongly associated with recurrence within a year in NMIBC. This scoring system, which relies on a very simple and fast peripheral blood cell subset phenotyping, was very predictive (>80%), even though the cohort was small. Because to date, no biomarker is validated for daily clinical practice, CD8-ILT scoring could be the first reliable prognosis tool for NMIBC recurrence. The frequency of endoscopic controls could so be adapted to the results of the test.

The invention claimed is:

1. A method for treating non-muscle invasive bladder cancer (NMIBC) in a patient, comprising: a step of measuring the proportion of CD8+T lymphocytes population expressing ILT-2 within the total population of CD8+T lymphocytes in a biological sample obtained from said patient, wherein when said proportion is of at least 34%, then the patient is classified as being at risk for NMIBC recurrence, and
    a step of treating the patient classified as being at risk for NMIBC recurrence with an appropriate therapy or NMIBC.

2. The method according to claim 1, wherein it is performed within a year after surgery of said non-muscle invasive bladder cancer in the patient.

3. The method according to claim 1, wherein the biological sample is a blood sample or a plasma sample.

4. The method according to claim 1, wherein the step of measuring the proportion of CD8+T lymphocytes population expressing ILT-2 within the total population of CD8+T lymphocytes is performed by flow cytometry.

5. The method according to claim 1, wherein said proportion of $CD8^+$ T lymphocytes is at least 35%.

6. The method according to claim 5, wherein said proportion of $CD8^+$ T lymphocytes is at least 37%.

7. The method according to claim 6, wherein said proportion of $CD8^+$ T lymphocytes is at least 38%.

8. The method according to claim 7, wherein said proportion of $CD8^+$ T lymphocytes is at least 39%.

9. The method according to claim 8, wherein said proportion of $CD8^+$ T lymphocytes is and at least 41%.

10. The method according to claim 1, wherein said therapy is selected from the group consisting of surgery, chemotherapy, Bacille Calmette-Guerin (BCG), and combinations thereof.

11. The method according to claim 1, wherein said therapy is transurethral resection.

* * * * *